(12) United States Patent
Pigott

(10) Patent No.: US 11,160,995 B2
(45) Date of Patent: Nov. 2, 2021

(54) VISUALIZING SCATTERED RADIATION IN AN OPERATING ROOM

(71) Applicant: John Pigott, Sylvania, OH (US)

(72) Inventor: John Pigott, Sylvania, OH (US)

( * ) Notice: Subject to any disclaimer, the term of this patent is extended or adjusted under 35 U.S.C. 154(b) by 0 days.

(21) Appl. No.: 16/897,710

(22) Filed: Jun. 10, 2020

(65) Prior Publication Data

US 2020/0391054 A1 Dec. 17, 2020

Related U.S. Application Data

(60) Provisional application No. 62/859,935, filed on Jun. 11, 2019.

(51) Int. Cl.
| | |
|---|---|
| *G01D 18/00* | (2006.01) |
| *A61N 5/10* | (2006.01) |
| *G01T 1/16* | (2006.01) |
| *A61B 6/10* | (2006.01) |

(52) U.S. Cl.
CPC .............. *A61N 5/1075* (2013.01); *G01T 1/16* (2013.01); *A61B 6/107* (2013.01)

(58) Field of Classification Search
CPC .................... A61N 5/1075; A61N 2005/1094; G01T 1/16; G01T 7/00; G01T 1/02; A61B 6/107; A61B 6/4441; A61B 6/547; A61B 6/02
See application file for complete search history.

(56) References Cited

U.S. PATENT DOCUMENTS

| | | | |
|---|---|---|---|
| 8,552,858 B2 | 10/2013 | Hohmann et al. | |
| 8,774,361 B2 | 7/2014 | Kargar et al. | |
| 2017/0220716 A1* | 8/2017 | Padoy | A61N 5/1075 |

OTHER PUBLICATIONS

Rodas et al., "Seeing is believing:increasing intraoperative awareness to scattered radiation in interventional procedures by combining augmented reality, Monte Carlo simulations and wireless dosimeters," International Journal of Computer Assisted Radiology and Surgery, 2015, vol. 10, pp. 1181-1191. (Year: 2015).*
Fluke Biomedical, 05-106 and 01-104 Bleeper mR and Bleeper III Personal Radiation Monitors, Dec. 2013.
Mediview, Tech Overview, https://mediview.com/our-tech/, Accessed May 22, 2020.
VascularNews, Working with Radiation is Like Keeping a Pet Tiger in Your Living Room, Sep. 2015.
VascularNews, Radiation Exposure During EVAR Causes DNA Damage in Operators, https://vascularnews.com/radiation-exposure-evar-dna-damage-operators/, Oct. 27, 2017.

(Continued)

*Primary Examiner* — Kiho Kim
(74) *Attorney, Agent, or Firm* — Standley Law Group LLP

(57) ABSTRACT

Systems and methods for providing a real time visualization of scattered radiation in an operating room are provided. A number of visualization devices such as augmented reality ("AR") tracking devices, electronic displays, or projection devices are in electronic communication with a controller and configured to display a visualization of scattered radiation. Position data is received from the position sensors associated with individuals in the operating room, the AR tracking devices, radiation producing medical equipment, or an operating table and the visualization is adjusted accordingly.

22 Claims, 16 Drawing Sheets
(9 of 16 Drawing Sheet(s) Filed in Color)

(56) References Cited

OTHER PUBLICATIONS

DI Cardiology, 5 Technologies to Reduce Cath Lab Radiation Exposure, https://www.dicardiology.com/article/5-technologies-reduce-cath-lab-radiation-exposure, Aug. 9, 2016.
American College of Cardiology, Highlights from SCAI 2014 CardioSource, WorldNews Interventions, Real-Time Radiation Monitoring Reduces Exposure to Patients and Interventionalists, https://www.acc.org/latest-in-cardiology/articles/2014/05/22/14/43/highlights-from-scai-2014, Aug. 22, 2014.
Kirkwood, M. et al., Southern Association for Vascular Surgery, Surgeon Education Decreases Radiation Dose in Complex Endovascular Procedures and Improved Patient Safety, Sep. 2013, pp. 715-721, vol. 58, No. 3.
VascularNews, Alarming Lack of Physician Awareness About Radiation Hazards Exposed, Jun. 2014.
New England Society for Vascular Surgery, Defining the Radiation 'Scatter Cloud' in the Interventional Suite, Nov. 2013.
Rehn, E., Linkoping University, Modeling of Scatter Radiation During Interventional X-Ray Procedures, Jun. 2015.

* cited by examiner

VISUALIZING SCATTERED RADIATION IN AN OPERATING ROOM

CROSS-REFERENCE TO RELATED APPLICATIONS

This application claims the benefit of U.S. Provisional Application Ser. No. 62/859,935 filed Jun. 11, 2019, the disclosures of which are hereby incorporated by reference as if fully restated herein.

TECHNICAL FIELD

Exemplary embodiments relate generally to systems and methods for visualizing scattered radiation, such as in an operating room.

BACKGROUND AND SUMMARY OF THE INVENTION

Many modern surgical procedures require the use of radiation producing equipment. For example, to reduce the invasiveness of surgery, small devices are often used in conjunction with imaging equipment. A more specific example is vascular surgery, where small devices are inserted into a patient's vascular system and imaging equipment is used to track device position and blood flow. As radiation is released from such machines, it encounters the patient and other objects, such as the operating table, and may scatter through some or all of the operating room. Being invisible to the human eye, radiation exposure zones are difficult to track. Repeated or extended exposure to even minimal amounts of radiation can result in health risks to operating room staff. Radiation shielding and protective equipment, while helpful, does not altogether eliminate such exposures.

It is known to provide radiation tracking devices to personnel in an operating room to assist with tracking radiation exposure. These radiation tracking devices may be checked periodically, such as once a month, to determine approximate exposure levels. As a general rule, personnel are encouraged to stay at least six feet away from radiation producing equipment, when possible, to minimize exposure. However, it is difficult for personnel to constantly and accurately determine their distance from the equipment, especially in the course of an operation on a patient. Furthermore, radiation intensity varies based on a number of factors which change the radiation intensity for a given location. Personnel might be able to make changes to their body positioning to reduce exposure if made aware of the location of the invisible and harmful radiation. Therefore, what is needed is a system and method for visualizing scattered radiation in an operating room.

Systems and methods for visualization of scattered radiation in an operating room are disclosed. Information may be provided regarding, for example without limitation, a type of radiation producing medical equipment device, patient height, and patient weight. The position of an operating table and the medical equipment device may be determined from position sensors. A visualization of the radiation scatter may be generated by a controller and provided at one or more visualization devices. The visualization devices may include augmented reality ("AR") tracking devices, electronic displays, and/or projection devices.

The visualization may be configured to appear fixed relative to the various visualization devices such that as personnel move about the operating room and/or change their gaze, the visualization is updated at their visualization device to appear to be in the same location. The location may comprise, for example without limitation, adjacent to radiation producing equipment, operating table, patient, some combination thereof, or the like. As the position of the operating table and/or medical equipment device is changed, the visualization may be updated. Each person in the operating room may be outfitted with a position tracking device. Alternatively, or additionally, various pieces of equipment in the operating room, such as but not limited to, the operating table, radiation producing equipment, and the like may be outfitted with position tracking devices. In this way, the position of such people and/or items may be tracked for updating the visualization. Multiple position devices may be utilized for a given person or piece of equipment. Updates to the visualization may be made in substantially real time.

The visualization may comprise a multi-layered cloud or sphere, though other forms such as, but not limited to, lines, shapes, text, color, or the like may be utilized in the alternative or in addition. Various areas of the visualization may be color coded, shape coded, marked with text, provided in certain densities or intensities, some combination thereof, or the like to indicate the danger level associated with expected radiation intensity for that area. In another exemplary embodiment, a single light may be increased in intensity or illuminance to indicate relatively higher relative radiation. Alternatively, or additionally, sounds may be emitted in varying tone, frequencies, amplitudes, some combination thereof, or the like as the personnel approach radiation producing equipment. Regardless, the visualization and/or audio feedback may provide personnel in the operating room with real time, qualitative type feedback regarding their expected level of danger. Personnel may use this feedback to limit their exposure level.

The visualization may be provided at a transparency level sufficient to permit the personnel to see the patient and equipment in the room while also viewing the visualization. By way of non-limiting example, transparency levels of 20% or under may be utilized.

In exemplary embodiments, at least some of the visualization devices may comprise radiation exposure tracking devices. Exposure data from such devices may be used to improve the accuracy of the visualization and/or track personnel exposure levels. Alternatively, or additionally, relative exposure may be tracked by position of the personnel while the radiation producing equipment is active. Regardless, exposures data may be recorded to calculate various exposure levels over time, predicted exposure levels, average exposure levels, some combination thereof or the like. Such data may be generated into one or more reports and/or provided as alerts, such as when a person approaches a periodic goal or threshold.

Further features and advantages of the systems and methods disclosed herein, as well as the structure and operation of various aspects of the present disclosure, are described in detail below with reference to the accompanying figures.

BRIEF DESCRIPTION OF THE DRAWINGS

The patent or application file contains at least one drawing executed in color. Copies of this patent or patent application with color drawing(s) will be provided by the Office upon request and payment of the necessary fee. In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
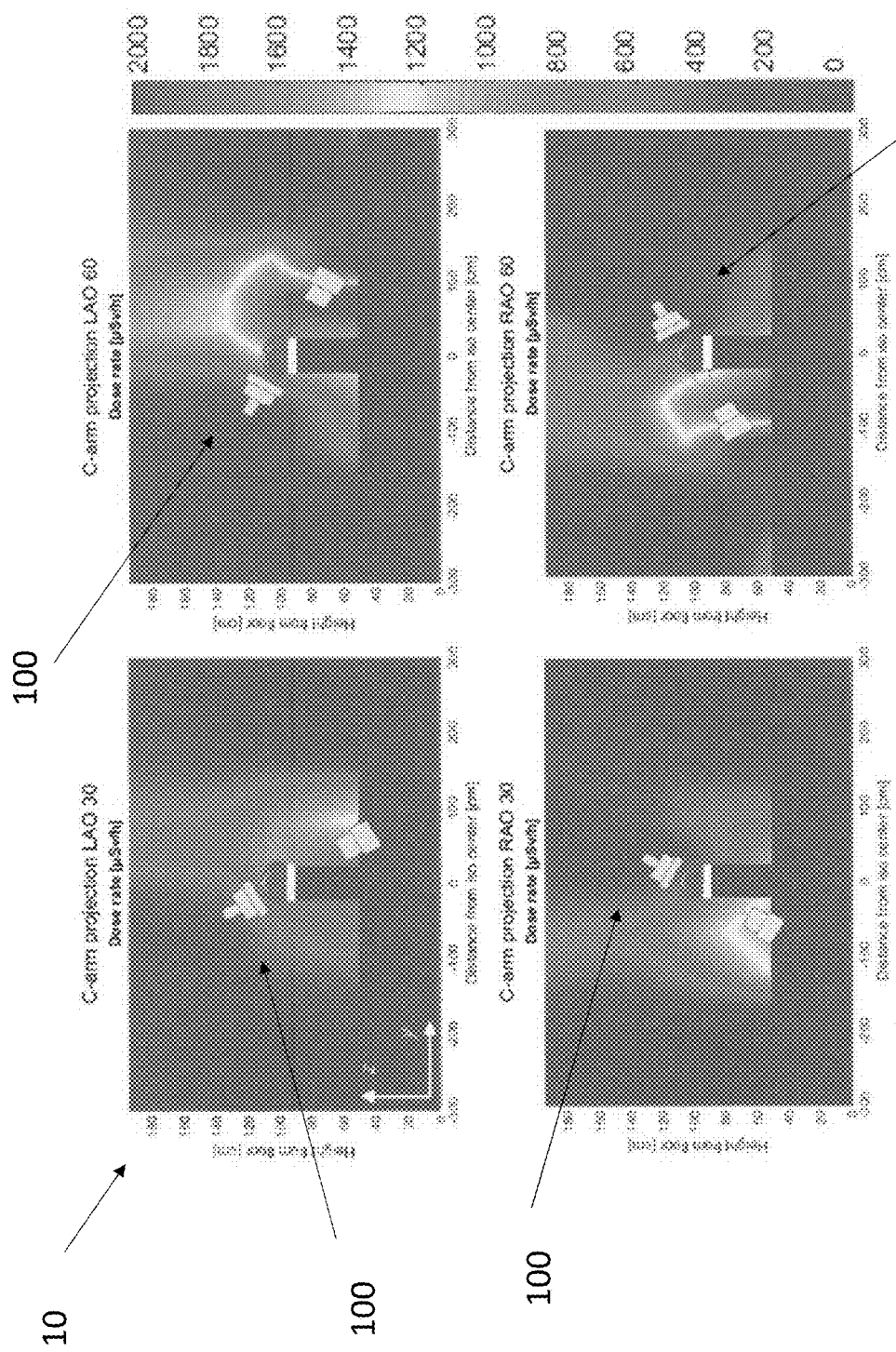
FIG. 1 is a plan view of an exemplary conventional, two-dimensional radiation scatter intensity diagram.
Figure 2:
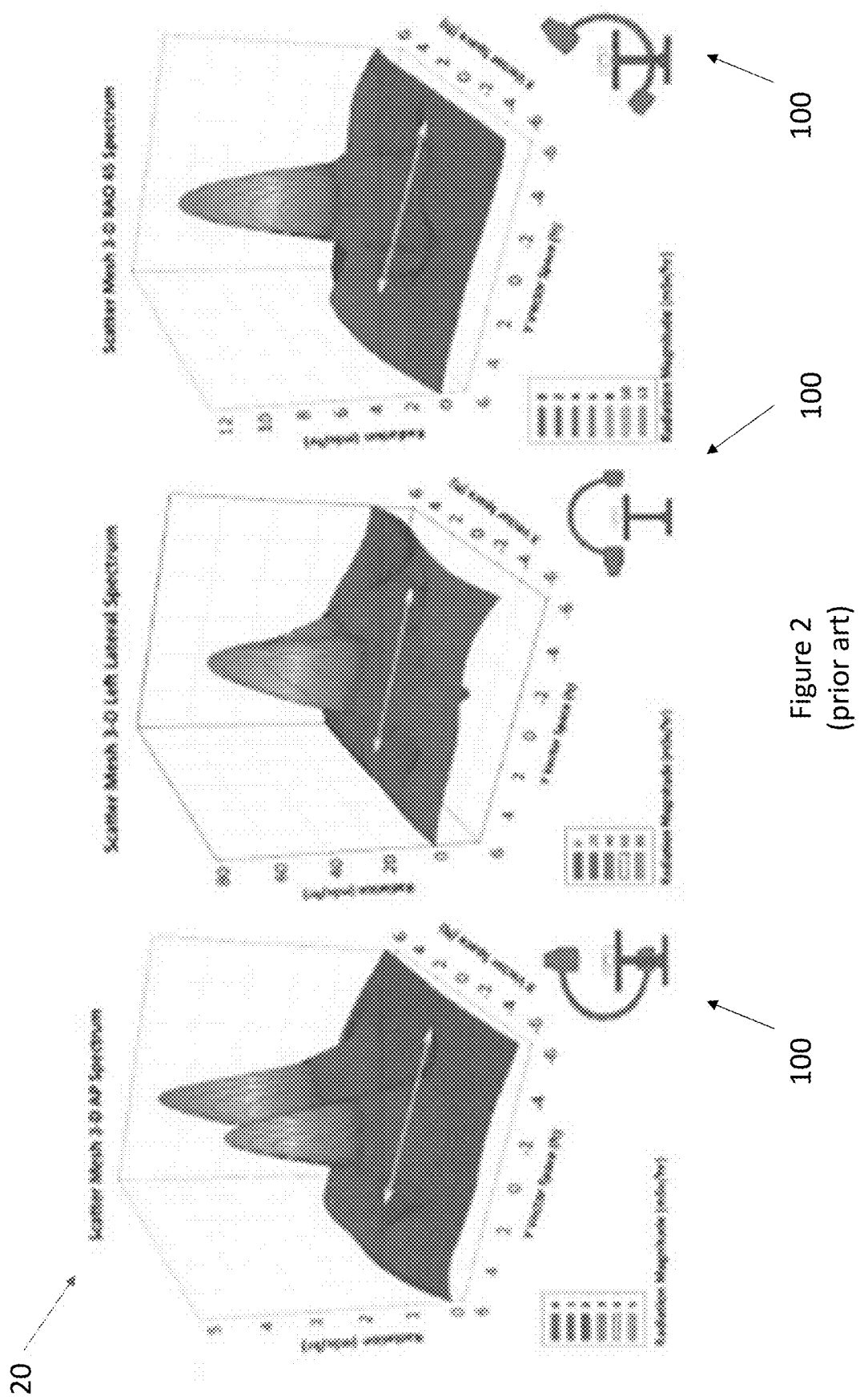
FIG. 2 is a perspective view of an exemplary conventional, three-dimensional radiation scatter intensity diagram.

FIG. 1 illustrates an exemplary, conventional two-dimensional radiation scatter intensity diagram 10. FIG. 2 illustrates an exemplary, conventional three-dimensional radiation intensity diagram 20. Such diagrams 10, 20 may be provided by manufacturers of radiation producing equipment 100 or other sources. The equipment 100 may comprise, without limitation, imaging devices. The diagrams 10, 20 may be specific to the type, brand, make, model, some combination thereof, or the like of the equipment 100. Multiple diagrams may be provided for various orientations, settings, some combination thereof, or the like of the equipment 100. The diagrams 10, 20 may be color coded to reflect the radiation intensity of a given area.

Figure 3:
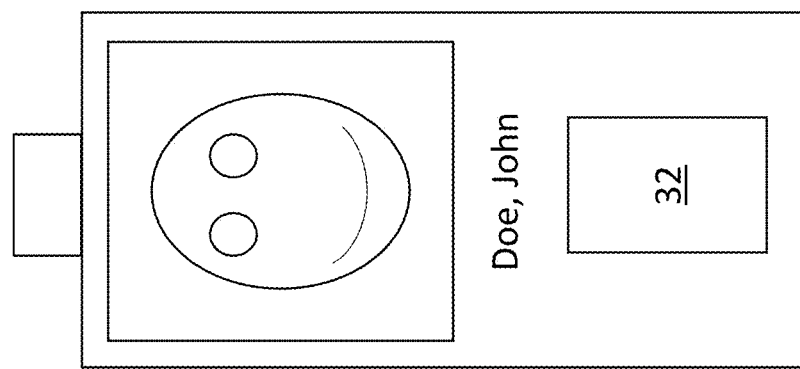
FIG. 3 is a front view an exemplary conventional radiation exposure tracking device.
Figure 3:

FIG. 3 illustrates an exemplary, conventional radiation tracking device 30. Typically, such devices 30 are provided as badges which may comprise identifying information such as photos, names, some combination thereof, or the like. The device 30 may comprise a radiation exposure measurement device 32. The radiation exposure measurement device 32 may comprise, for example without limitation, a dosimeter, Geiger counter, alpha radiation survey meter, dose rate meter, some combination thereof, or the like. Such devices 30 may be worn by personnel in an operating room. The devices 30 may be periodically checked, such as once a month, to determine radiation exposure.

Figure 4:
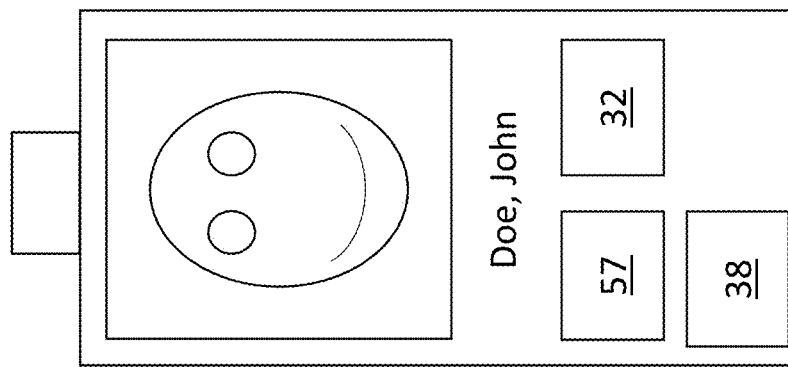
FIG. 4 is a front view of an exemplary tracking device in accordance with the present invention.
Figure 4:

FIG. 4 illustrates an exemplary tracking device 36. The tracking device 36 may comprise one or more of the radiation exposure measurement devices 32, though such is not required. The tracking device 36 may comprise one or more position tracking devices 57 configured to track the location and/or orientation of the tracking device 36. The position tracking devices 57 may comprise a GPS device, wi-fi device, near field communication device, accelerometer, gyroscope, angle sensor, magnetometer, some combination thereof, or the like. In this way, the location and/or radiation exposure of the personnel wearing the tracking device 36 may be monitored. The tracking device 36 may comprise a network connectivity device 38 configured to place the tracking device 36 in communication with one or more remote devices, such as but not limited to, a controller 56. Data regarding location and/or radiation exposure may be transmitted to the controller 56 by way of the network connectivity device 38. The location and/or radiation exposure may be monitored and/or transmitted continuously or periodically.

In other exemplary embodiments, the tracking devices 36 may comprise the position tracking device 57 and/or the network connectivity device 38, but not the radiation exposure measurement device 32.

A number of tracking devices 36 and/or radiation tracking devices 30 may be utilized on each person in the operating room in accordance with the present invention. In exemplary embodiments, without limitation, each person in the operating room may be outfitted with tracking devices 36 and/or radiation tracking devices 30 on different parts of their body. For example, without limitation, such devices 36, 30 may be positioned at the person's head, neck, torso, wrists, ankles, arms, legs, some combination thereof or the like to measure the position and/or radiation exposure of these individual parts of the person's body. Often, a particular area of the person may be exposed to a different level of relative radiation for a different period of time than other areas of the person's body. For example, without limitation, a surgeon's hands and/or eyes may be exposed to higher levels of relative radiation for longer periods of time as the surgeon may be unable to move his or her hands when performing a procedure. By using multiple tracking devices 32, distance from the equipment 100, relative exposure levels, and other data specific to certain parts of the body may be determined and/or tracked.

Distance, relative exposure levels, and other data may be tracked and/or reported in real time or may be stored for post-operative review. For example, without limitation, distance from the equipment 100, location, relative exposure levels, and other data may be monitored and/or reported in real time, post-operative, every few seconds, some combination thereof, or the like. By way of a non-limiting example, as used herein the term real time or substantially real time may account for transmission times, temporary storage times, data processing times, lag times, some combination thereof, or the like.

Figure 5:
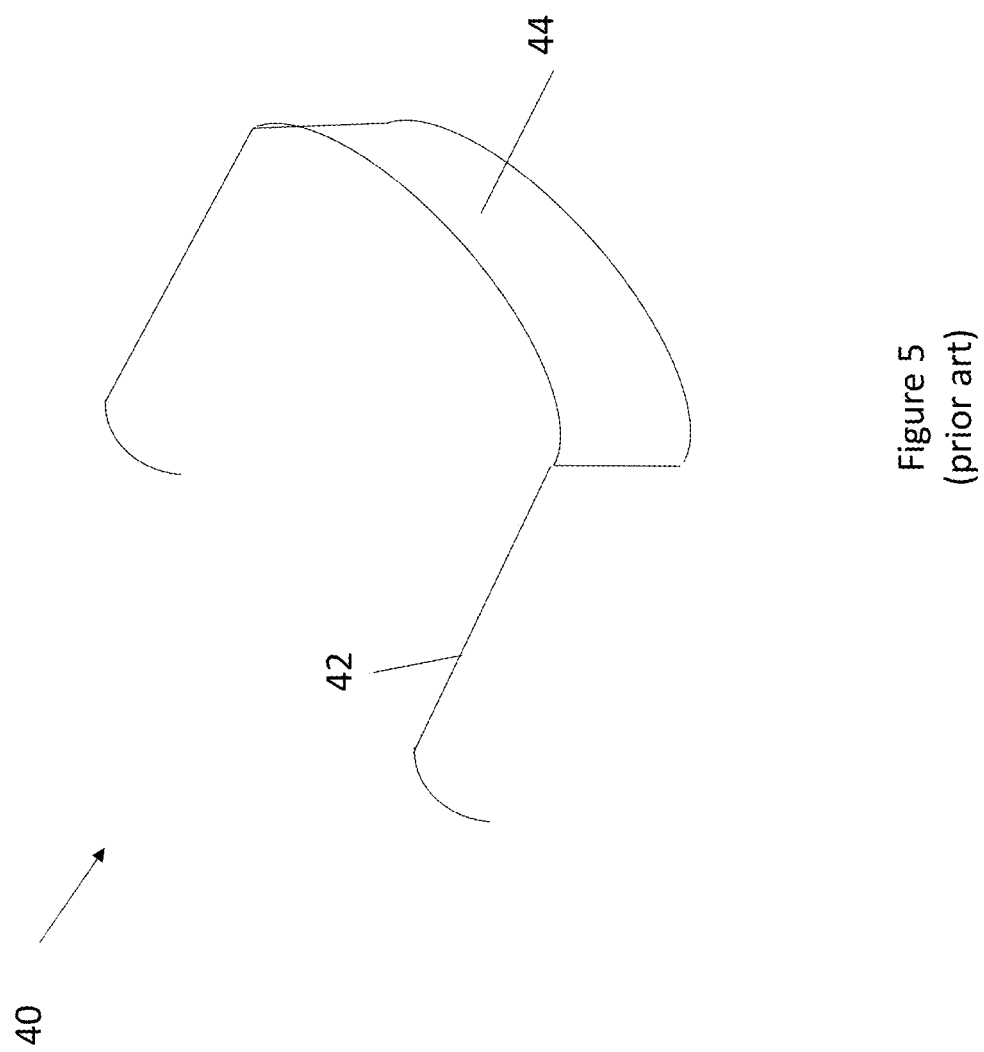
FIG. 5 is a perspective view of an exemplary conventional augmented reality device.

FIG. 5 illustrates an exemplary, conventional augmented reality ("AR") device 40. The AR device 40 may comprise one or more body attachment portions 42. The body attachment portions 42 may comprise head bands, frames, contact lenses, some combination thereof, or the like. The AR device 40 may comprise one or more display portions 44. The display portion 44 may comprise a transparent or translucent material. The display portions 44 may be configured to display one or more images. The display portions 44 may comprise one or more screens, shields, glasses, display surfaces, contact lenses, glasses lenses, some combination thereof, or the like. Examples of such AR devices 40 include, but are not limited to, Glass® from Google® (https://www.google.com/glass/start/), HoloLens® from Microsoft® (https://www.microsoft.com/en-us/hololens). The display portion 44 may be configured to display images in a way which permits the user to see the real world beyond the display portion 44 such that the images are overlaid onto the real world.

Figure 6:
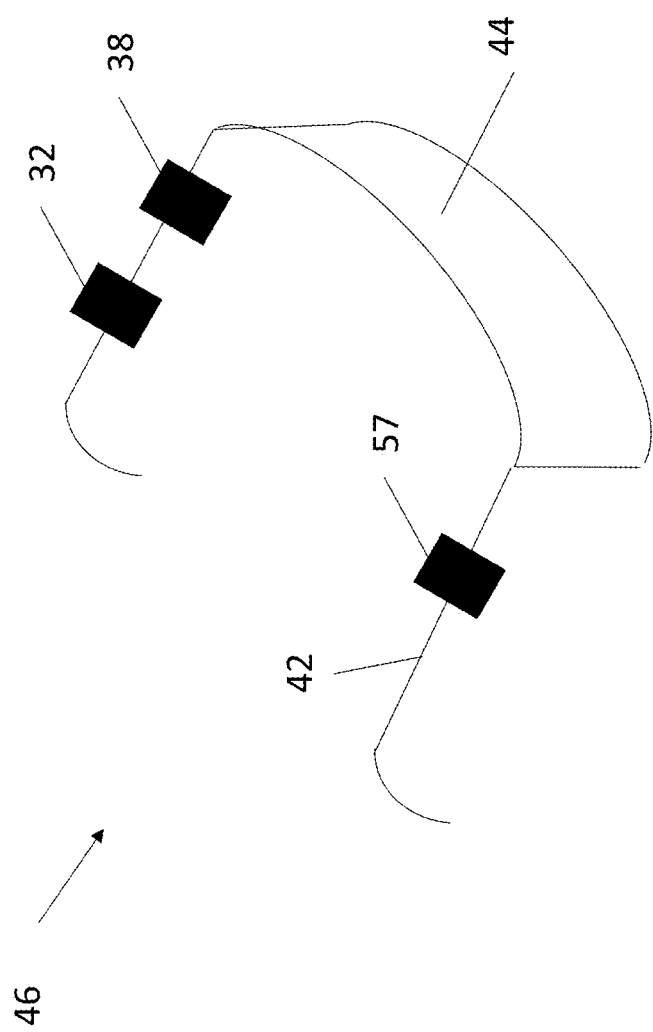
FIG. 6 is a perspective view of an exemplary augmented reality tracking device in accordance with the present invention.
Figure 7:
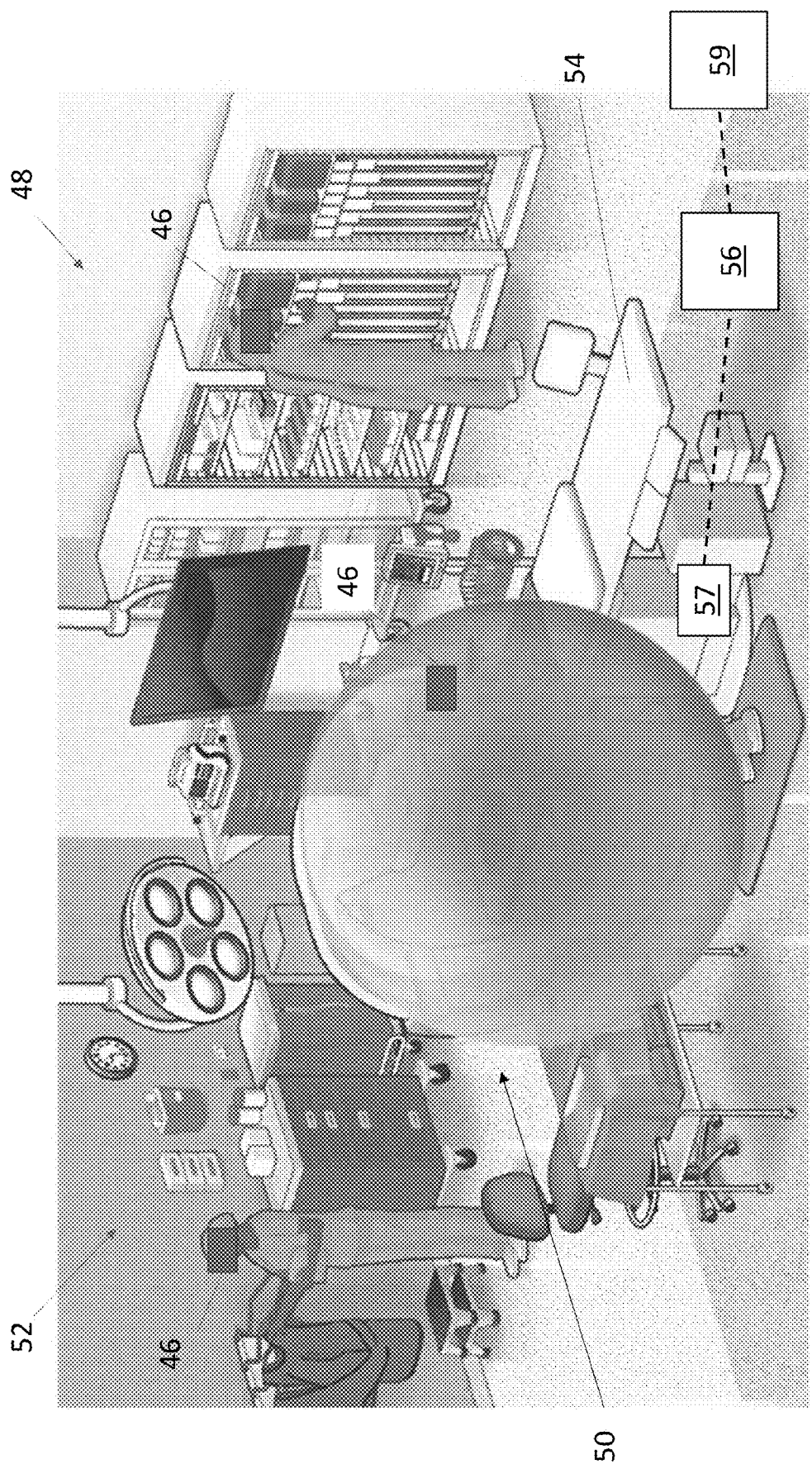
FIG. 7 is a perspective view of an operating room with an exemplary radiation scatter visualization using an exemplary augmented reality system in accordance with the present invention.
Figure 8:
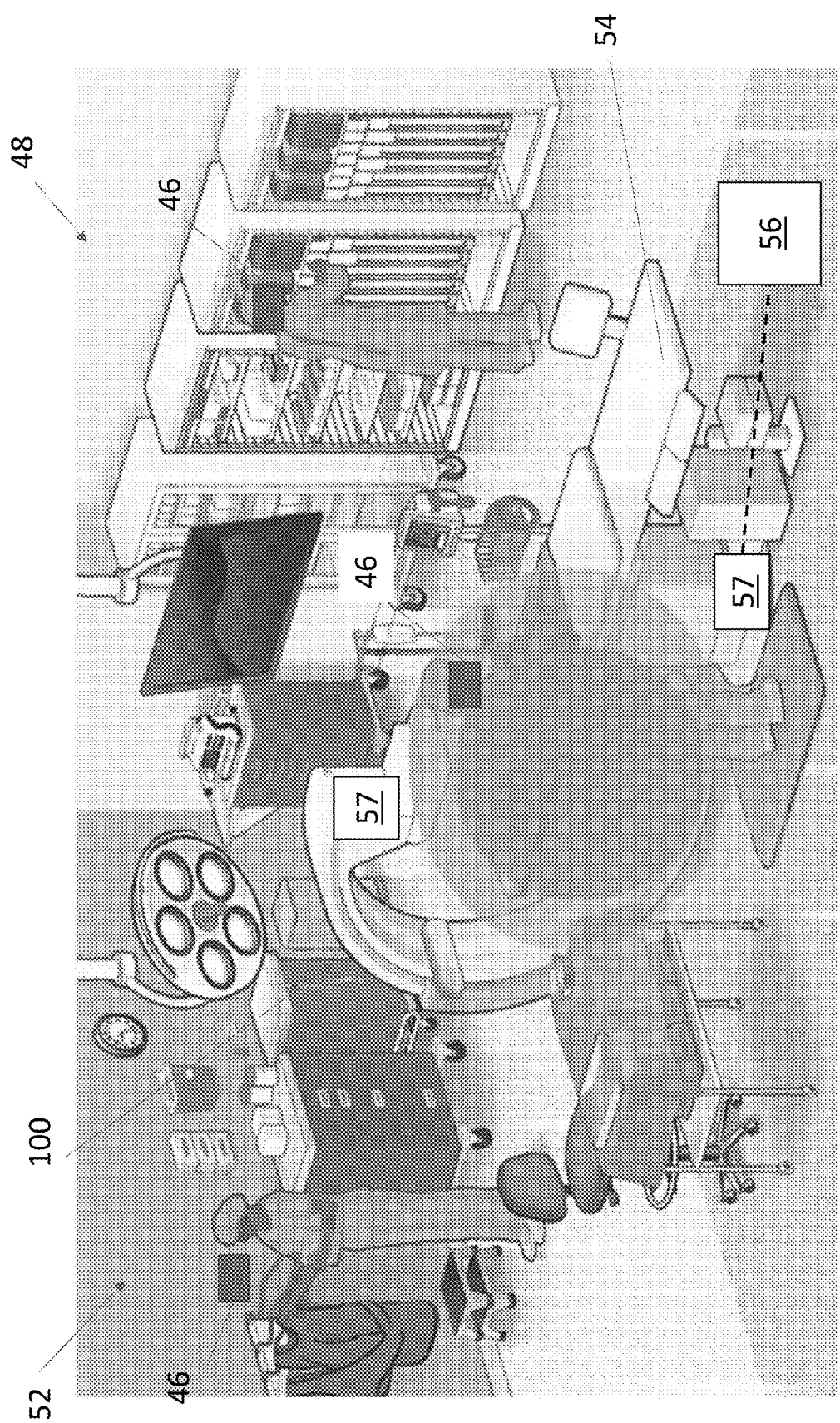
FIG. 8 is a perspective view of the operating room of FIG. 7 with another exemplary radiation scatter visualization.

FIG. 6 illustrates an exemplary AR tracking device 46. The AR tracking device 46 may comprise the radiation exposure measurement device 32. The AR tracking device 46 may, alternatively or additionally, comprise one or more position tracking device 57 configured to track the location and/or orientation of the AR tracking device 46. In exemplary embodiments, the position tracking device 57 may be configured to track the orientation of the user's head, and therefore their gaze. In this way, the AR tracking device 46 may be configured to track the location and/or radiation exposure of personnel wearing the AR tracking device 46 while providing visual images to said person.

The AR tracking device 46 may comprise the network connectivity device 38. The location and/or radiation exposure may be monitored and/or transmitted continuously or periodically to remote devices, such as but not limited to, the controller 56.

FIG. 7 through FIG. 10 illustrates exemplary operating rooms 52 with exemplary augmented reality systems 48. Personnel in the operating room 52 may be outfitted with the AR tracking device 46. The AR tracking device 46 may be configured to display a radiation scatter visualization 50 at the display portions 44 of the AR tracking devices 46 worn by each person. FIGS. 7 through 10 illustrate exemplary embodiments of the visualization 50 as it may appear to an individual wearing the AR tracking device 46. However, the visualization 50 may be displayed in the context of the user's position and/or gaze. Stated another way, FIGS. 7 through 10 illustrate what a user observes when wearing the AR tracking device 46 from a perspective view of the operating room 52. The user may see the surgeon in the middle of the visualization 50 and others off to the sides of the visualization 50. The surgeon in the middle may see the visualization 50 all about them while looking at a patient on the operating table 54.

The visualization 50 may be generated and updated, at least in part, by a controller 56. The controller 56 may be configured to utilize one or more reference or registration points to virtually affix the visualization 50 relative to the personnel in the room such that the visualization 50 appears fixed as persons wearing the AR tracking devices 46 move about the room. The visualization 50, for example without limitation, may be virtually affixed relative to the equipment 100, the operating table 54, the patient, some combination thereof, or the like.

In exemplary embodiments, without limitation, the controller 56 may be configured to process data stored in memory of a two or three-dimensional radiation intensity diagram 10,20, underlying data regarding the same, or the like, for the particular equipment 100 being used in the room, along with other inputted data such as the patient's body data, surgery table 54 height location data, etc., as further explained below. The controller 56 may be located in the operating room 52 or remote therefrom. The controller 56 may be in wired and/or wireless electronic communication with each AR tracking device 46, device 30, and/or tracking device 36 in the operating room 52. The visualization 50 may be updated at the various AR tracking devices 46 by the controller 56 periodically or continuously. The visualization 50 may be updated in substantially real time, such as but not limited to, as data is received and processed accounting for normal delays due to transmission time, processing time, and the like.

The visualization 50 may comprise one or more shapes, text, lines, some combination thereof, or the like of the same or various types to represent the intensity of the radiation. In exemplary embodiments, the visualization 50 may comprise a multi-layered cloud or sphere, though any form of the visualization may be utilized. For example, without limitation, the visualization 50 may comprise a first color representing a high level of relative radiation intensity, a second color representing a medium level of relative radiation intensity, and a third color representing a low level of relative radiation intensity. The first color, for example without limitation, may comprise a shade of red, the second color a shade of orange, and the third color a shade of yellow. As another example, without limitation the first color may comprise a shade of red, the second color a shade of yellow, and the third color a shade of green. Any color, or combination of colors may be utilized.

As another example, the visualization 50 may comprise a multi-layered cloud or sphere where certain shapes are displayed at a first density to represent a low level of relative radiation intensity, a second density to represent a medium level of relative radiation intensity, and a third density to represent a high level of relative radiation intensity.

Any number of layers, colors, shapes, lines, text, some combination thereof, or the like may be utilized. Each change in layer, color, shape, line, text, some combination thereof, or the like may correspond with a change in level of relative radiation intensity. The visualization 50 may be displayed at a transparency sufficient to provide visibility of the patient and/or equipment through the visualization 50 yet of adequate opaqueness to call the visualization 50 to the user's attention. An exemplary transparency is at or below 20%, though any percentage may be utilized.

The various layers of the visualization 50 may be visible simultaneously such that the user can see each layer of the visualization 50. Alternatively, each layer of the visualization 50 may be visible only as the user approaches and/or enters the layer of the visualization 50.

As yet another example, without limitation, the visualization 50 may comprise one or more lights of monochromatic or multiple colors which becomes brighter or otherwise more intense as a user approaches the machine 100 or other area of higher relative radiation intensity. The one or more lights may be of monochromatic or multiple colors which becomes dimmer or otherwise less intense as a user steps away from the machine 100 or moves into areas of lower relative radiation intensity.

Alternatively, or additionally, one or more speakers 59 may be provided. The speakers 59 may be in electronic communication with the controller 56. The controller 56 may be configured to cause the speakers 59 to emit an audible tone(s) or message(s) regarding relative radiation intensity. For example, without limitation, the tones emitted may increase or otherwise differ in tone, frequency, pitch, amplitude, some combination thereof, or the like as the user approaches areas of relatively higher radiation intensity and decrease as the user approaches areas of relatively lower radiation intensity. Audible messages regarding the relative radiation intensity, or the like may be emitted.

Each AR tracking device 46 may be configured to provide a visualization 50 of the scattered radiation specific to the location and/or direction of gaze of the person wearing the AR tracking device 46. Personnel may move about the operating room 52 and/or redirect their gaze and be provided with a substantially real-time update of the visualization 50 while still able to view the patient, the equipment 100, the table 54, other equipment, and otherwise perform their duties. In this way, personnel may be appraised of at least the approximate level of relative radiation intensity in a given area in the room. Personnel may use the visualization 50 as a guide for adjusting their position within the operating room 52, where possible, to minimize their exposure. For example, without limitation, a surgeon may lean backwards when activating the equipment 100 to minimize exposure. As another example, without limitation, an anesthesiologist who may not need to be physically close to the patient to perform his or her duties may position themselves outside of the visualization 50 to minimize his or her exposure. As yet another example, without limitation, a nurse may pull his or her hands away from the patient when the equipment 100 is active to move their hands from a relatively high to a relatively low area of relative radiation intensity.

The controller 56 may be configured to accept user input such as, but not limited to, at a touch screen interface, mouse, keyboard, voice recognition interface, some combination thereof, or the like. User input may include specification information for the machine 100, height of the patient, weight of the patient, radiation scatter, radiation intensity, radiation type, machine 100 settings, user preferences, some combination thereof, or the like. The controller 56 may comprise, or may receive, data regarding radiation intensity such as, but not limited to, data comprising or derived from the diagrams 10, 20 and/or other information provided from the manufacturer of the equipment 100, radiation exposure measurement device 32, other sources, some combination thereof, or the like. The controller 56 may extract at least some of this information from the equipment 100. Alternatively, or additionally, at least some of this information may be provided by user input and/or via one or more memory ports, wired or wireless network communication, some combination thereof, or the like. The controller 56 may be configured to adjust the visualization 50 based on the input. Where no input is provided and/or found, default settings may be used. The default setting may be based on averages, conservative measures, margins of safety, industry standards, some combination thereof, or the like.

Figure 9:
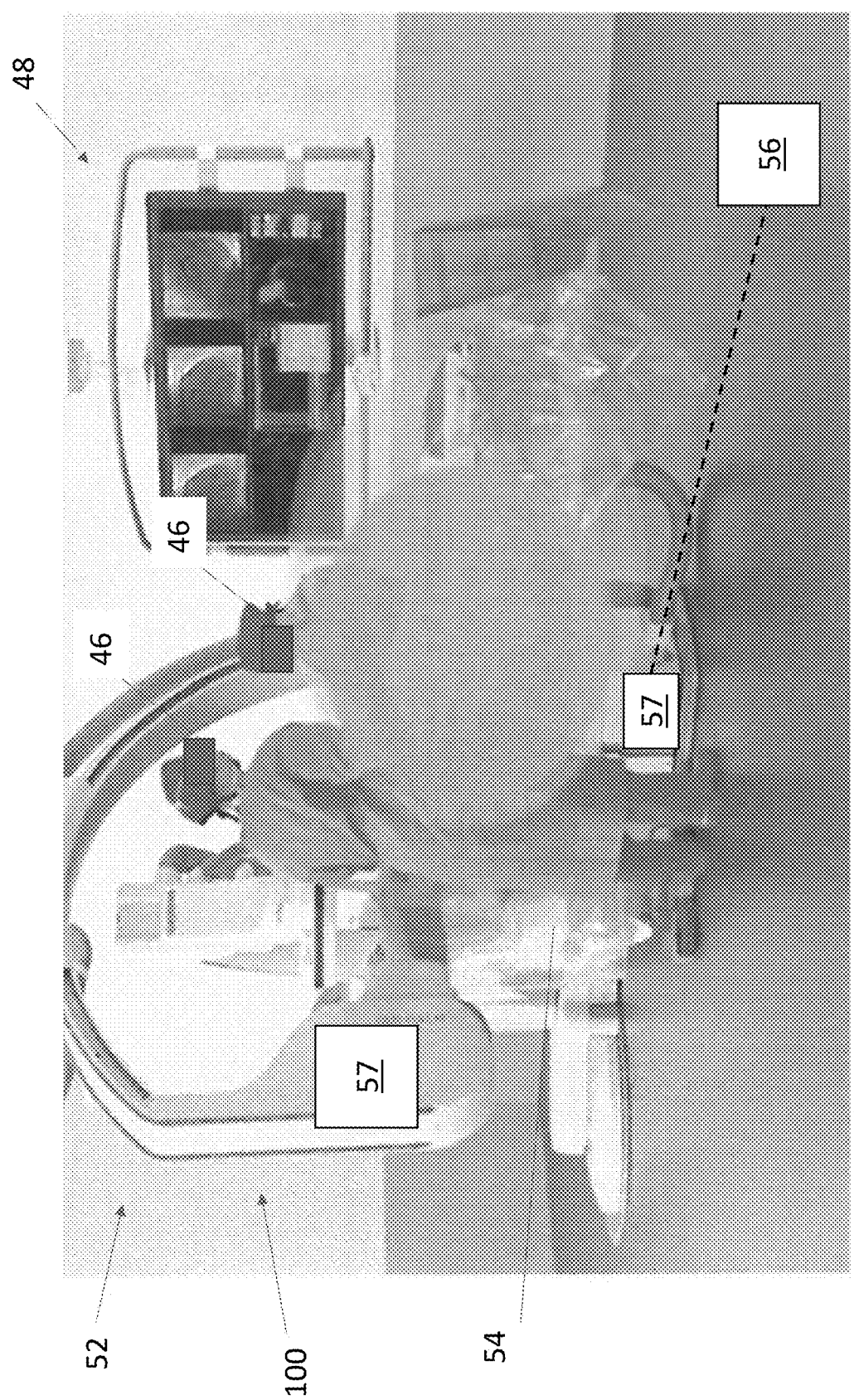
FIG. 9 is a perspective view of another exemplary operating room with another exemplary radiation scatter visualization for the augmented reality system of FIG. 7.
Figure 10:
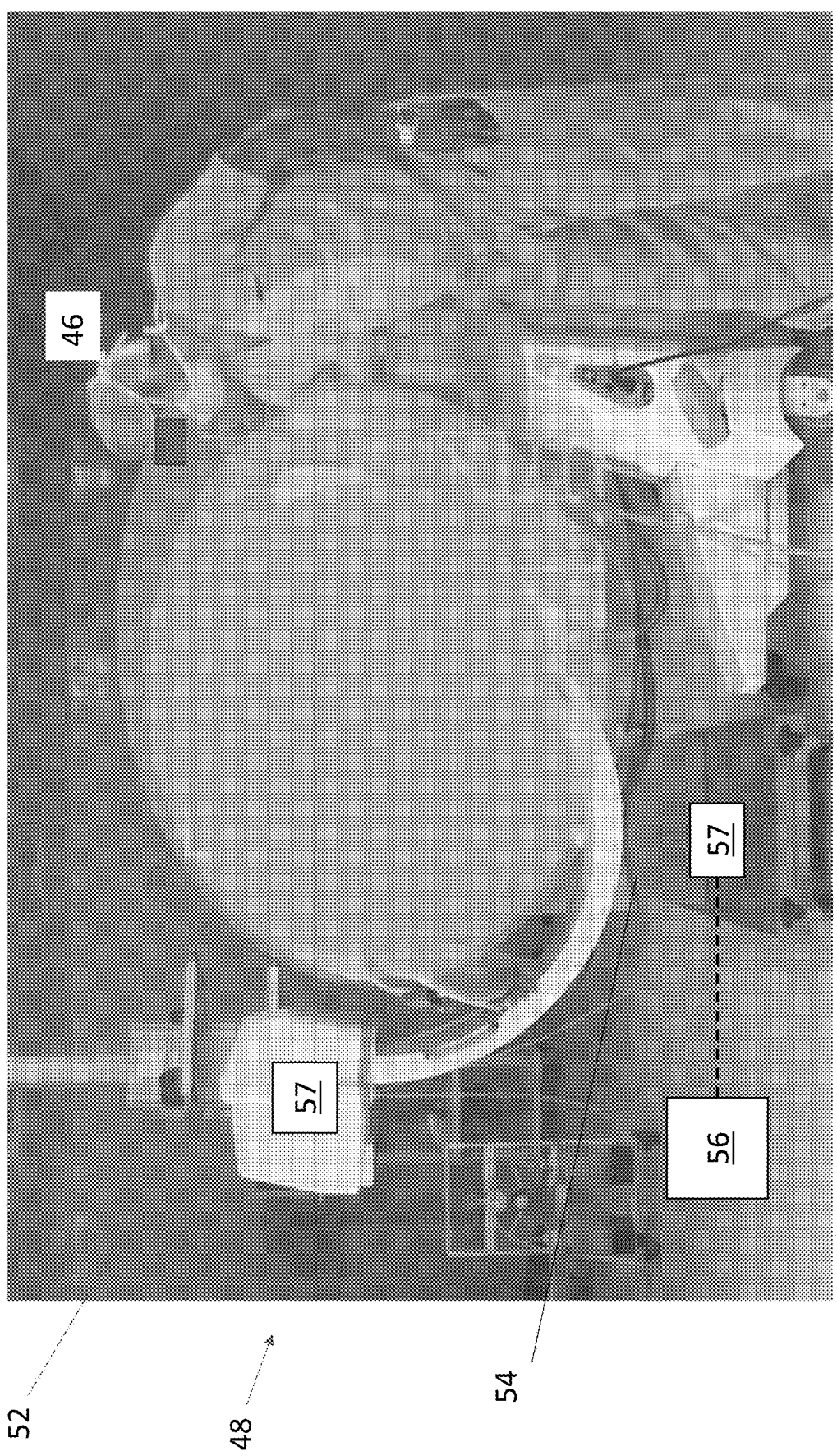
FIG. 10 is a perspective view of another exemplary operating room with another exemplary radiation scatter visualization for the augmented reality system of FIG. 7.

The controller 56 may be configured to adjust the visualization 50 based on the position of the equipment 100. For example, without limitation, the equipment 100 may be raised, lowered, rotated, moved, swiveled, some combination thereof, or the like to perform various procedures. The equipment 100 may comprise one or more position tracking devices 57 configured to track the location and/or orientation of the equipment 100. The position tracking devices 57 may be in electronic communication with the controller 56. The controller 56 may be configured to adjust the visualization 50 based on the position of the equipment 100. For example, FIG. 9 and FIG. 10 illustrates the machine 100 in a side orientation with the resulting visualization 50 skewed to the opposing side.

In exemplary embodiments, the operating table 54 may comprise one or more position tracking devices 57 configured to track the location and/or orientation of the operating table 54. The position tracking devices 57 may be in electronic communication with the controller 56. The controller 56 may be configured to adjust the visualization 50 based on the position of the operating table 54.

As another example, the equipment 100 and/or the table 54 may be moved about the operating room 52 to perform various tasks. The position of the visualization 50 may be moved with the equipment 100 and/or the table 54.

In exemplary embodiments, the controller 56 may be configured to receive radiation exposure data from the radiation exposure measurement devices 32. The radiation exposure measurement devices 32 may be provided at the radiation tracking devices 30, the tracking devices 36, the AR tracking devices 46, some combination thereof, or the like. In exemplary embodiments, data from the radiation exposure measurement devices 32 may be used to validate and/or improve the visualization 50. The visualization 50 may provide qualitative type feedback while the radiation exposure measurement devices 32 may provide quantitative type feedback. Alternatively, or additionally, the radiation exposure data may be used to track personnel exposure levels. Radiation exposure data collected may be specific to certain parts of the body, in exemplary embodiments, and may be recoded as such.

Figure 11:
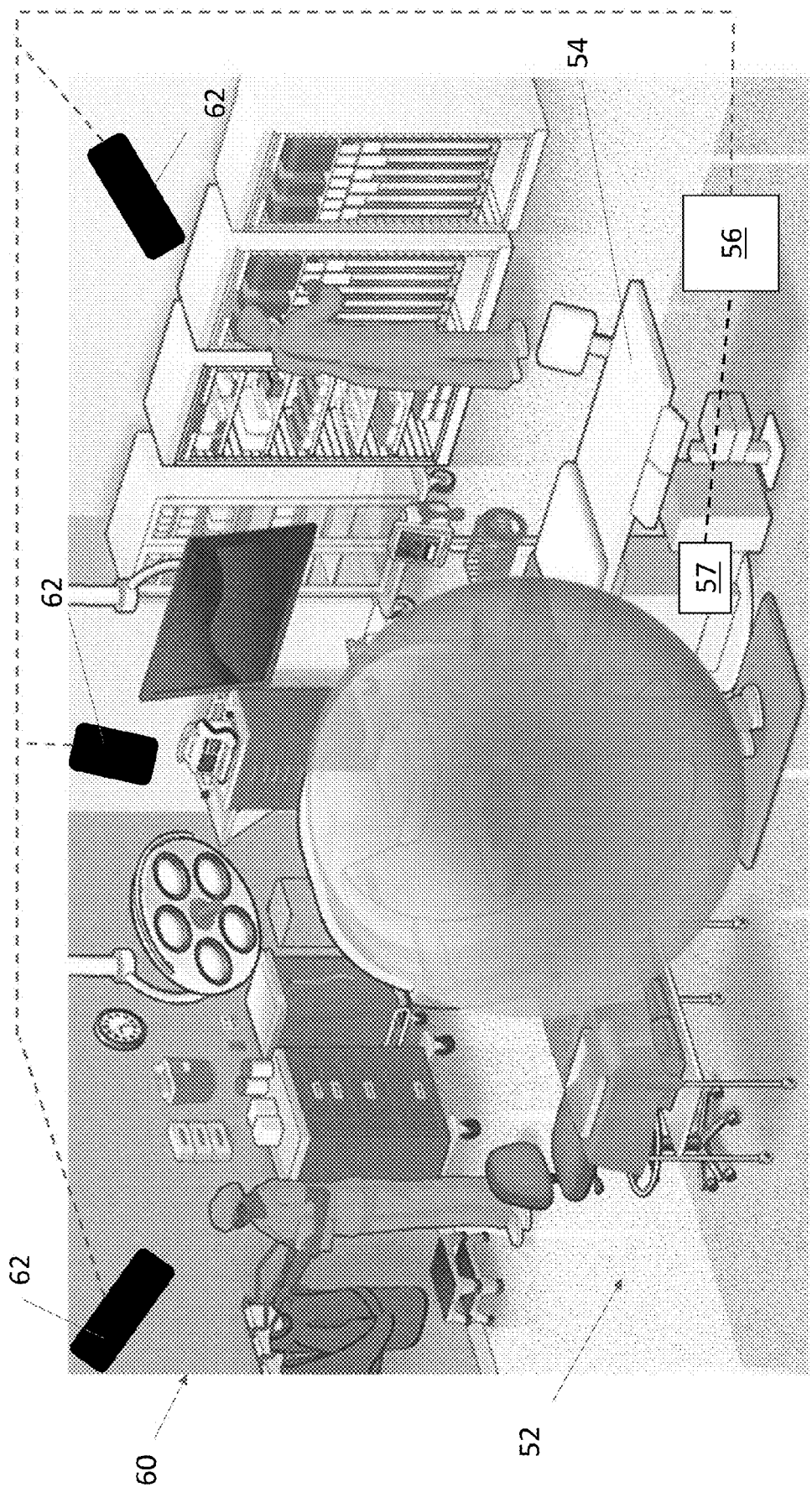
FIG. 11 is a perspective view of the operating room and visualization of FIG. 7 with an exemplary projection system in accordance with the present invention.

FIG. 11 illustrates an exemplary projection system 60 for providing the visualization 50. One or more projection devices 62 may be provided in the operating room 52. The projection devices 62 may be in electronic communication with the controller 56. The projection devices 62 may be configured to project the visualization 50 within the operating room 52. The projection devices 60 may be configured to provide a three-dimensional or two-dimensional image which is viewable with or without other visual aid. For example, without limitation, the projection system 60 may utilize laser plasma technology, Pepper's Ghost effect, fan holograms, light field displays, lasers and mirrors, no-logram technology, hologram technology, 3D volumetric technology, projection mapping technology, some combination thereof, or the like. The resulting visualization 50 may be provided in three-dimensions, or provided in two-dimensions with effects to make it appear three-dimensional to the viewer. The visualizations 50 of the radiation scatter in the room may be shown very accurately in one embodiment of the system of the present invention, or may be shown as informed approximations in another embodiment of the present invention, dependent upon how much data the user inputs into the system about the room, table 54, patient, equipment 100, and other factors affecting the scatter.

Figure 12:
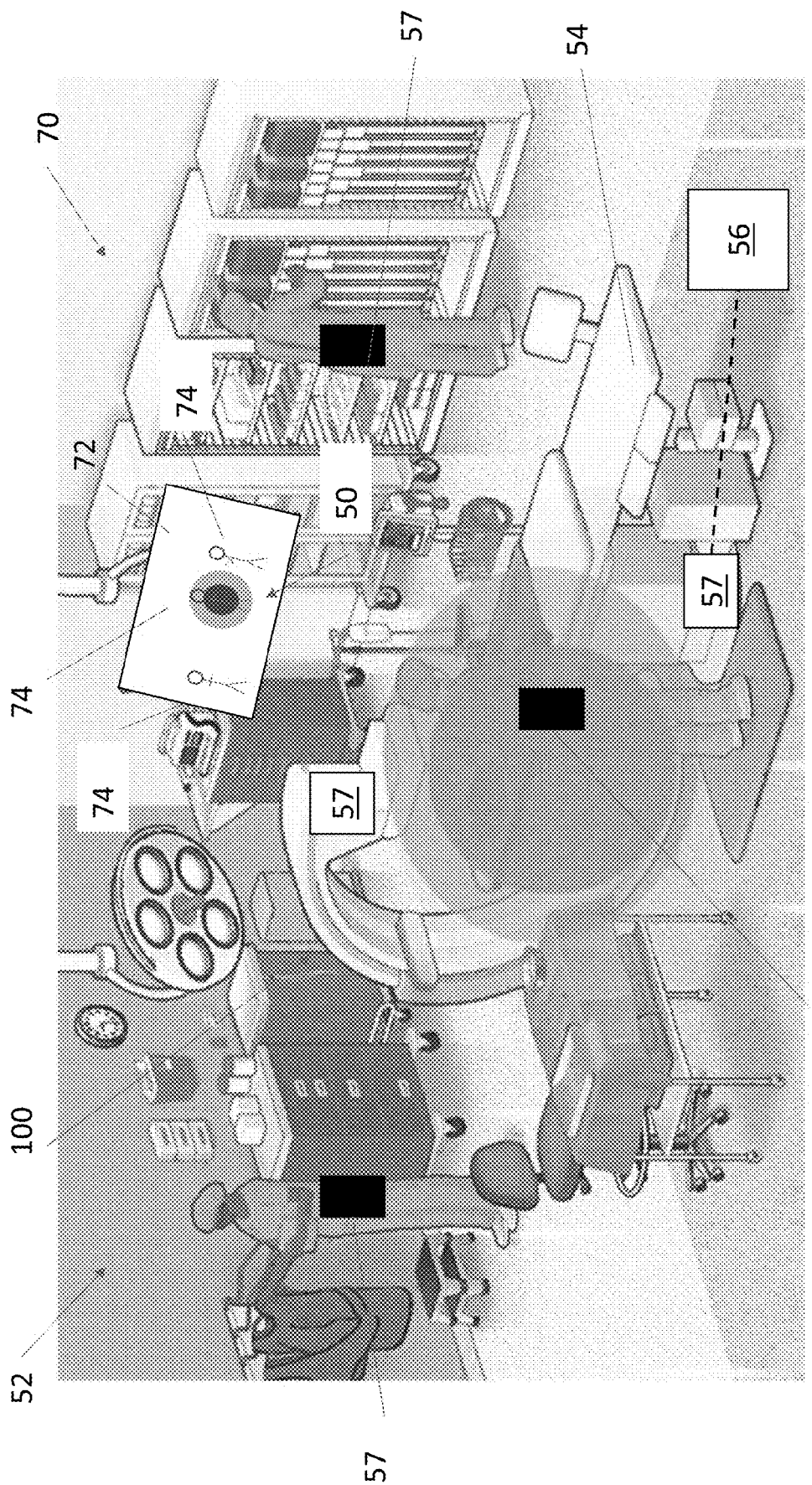
FIG. 12 is a perspective view of the operating room and visualization of FIG. 7 with an exemplary electronic display system in accordance with the present invention.

FIG. 12 illustrates an exemplary electronic display system 70 for providing the visualization 50. One or more such electronic displays 72 may be located at the operating room 52, though such is not required. Each electronic display 72 may be in electronic communication with the controller 56. The controller 56 may be configured to generate the visualization 50 at each electronic display 72. The controller 56 may be further configured to generate a representation of the personnel 74 in the operating room 52 at the electronic display 72. In this way, the personnel may reference their representation 74 on the electronic display 72 relative to the visualization 50 to get an estimation of the radiation intensity where they are located. The representations 74 may comprise names, images, or other identifying information for the person.

The location of the personnel may be provided by way of position tracking devices 57 provided to each person. The position tracking devices 57 may be provided with the tracking devices 36, the AR tracking devices 46, as a standalone device, some combination thereof, or the like. The relative radiation intensity exposure, as determined by the personnel's distance from the equipment 100 for example, may be tracked based on position readings from the position tracking devices 57.

Figure 13:
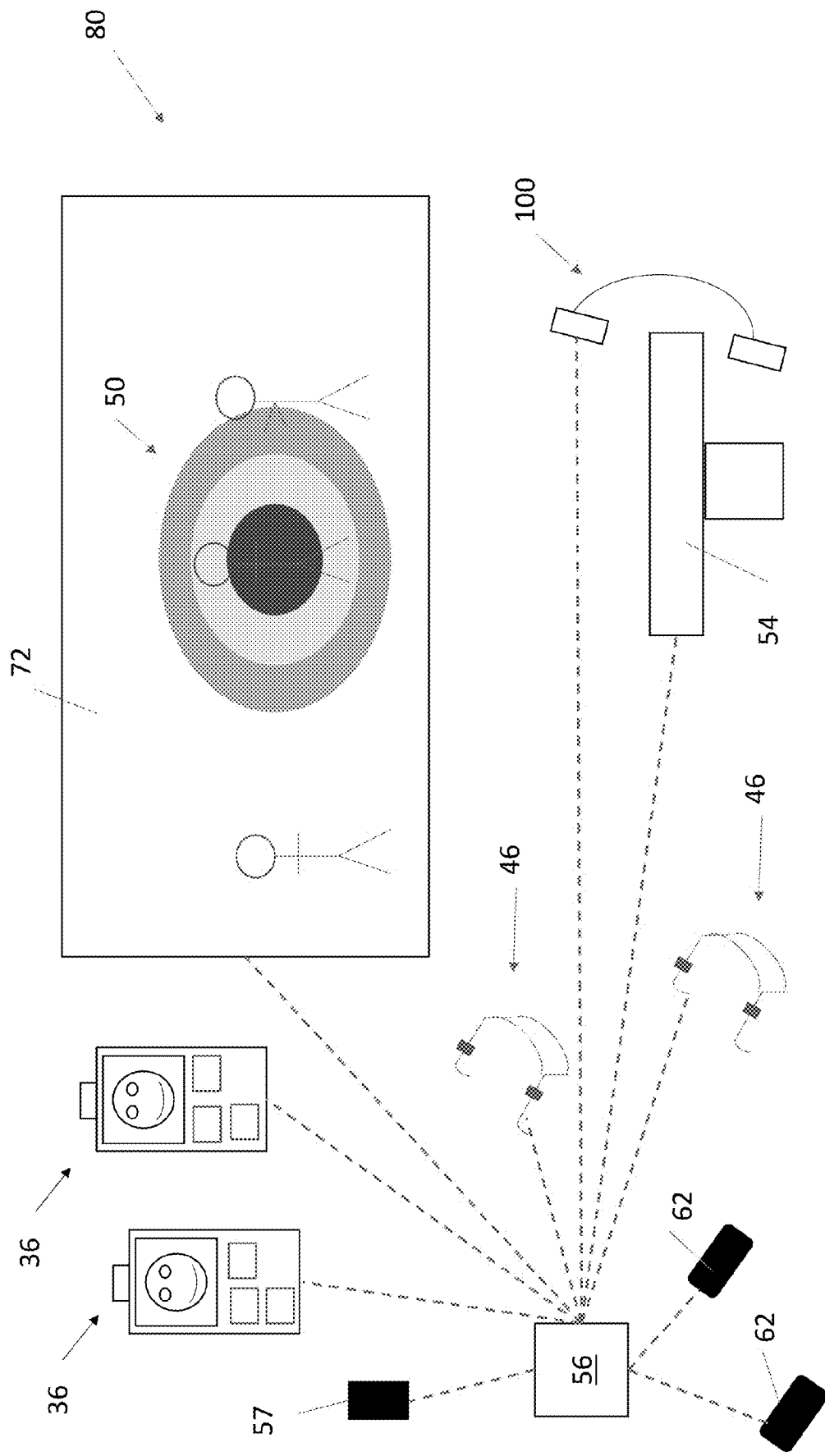
FIG. 13 is a simplified system diagram of an exemplary combined visualization system in accordance with the present invention.

FIG. 13 illustrates an exemplary combined system 80. The combined system 80 may utilize one or more of the tracking devices 36, the AR tracking devices 46, the electronic display 72, position tracking device 57, and the projection devices 62, in any combination and number. In this way, the combined system 50 may be provided at the AR tracking devices 46, the electronic display 72, and/or projected within the operating room 52.

Figure 14:
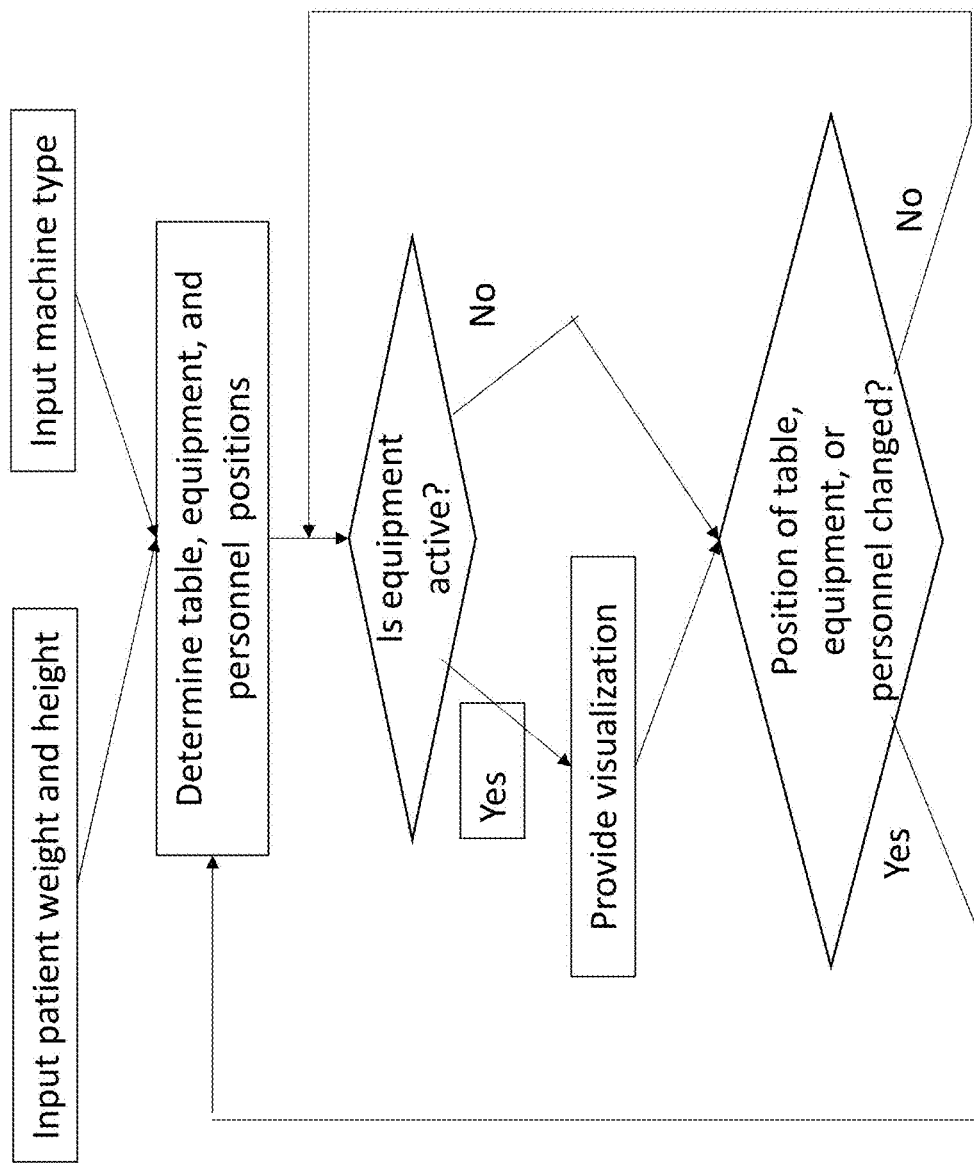
FIG. 14 is a flow chart with exemplary logic for operating the various visualization systems in accordance with the present invention.

FIG. 14 illustrates a flow chart with exemplary logic for providing the visualization 50. User input regarding the patient height, the patient weight, and the type of machines 100 may be provided to the controller 56. The position of the table 54 may be determined. The position of the equipment 100 may be determined. The position of the table 54 and/or the machine 100 may be determined by way of the respective position devices 57. The position of the personnel may be determined. The position of the personnel may be determined by way of position tracking devices 57, the tracking devices 36, and/or the AR tracking devices 46. The visualization 50 may be generated. The visualization 50 may be provided at each of the AR tracking devices 46, the electronic displays 72, and/or the projection devices 62 within the operating room 52. The visualization 50 may be updated as the position of the table 54, machine 100, and/or personnel changes.

Figure 15B:
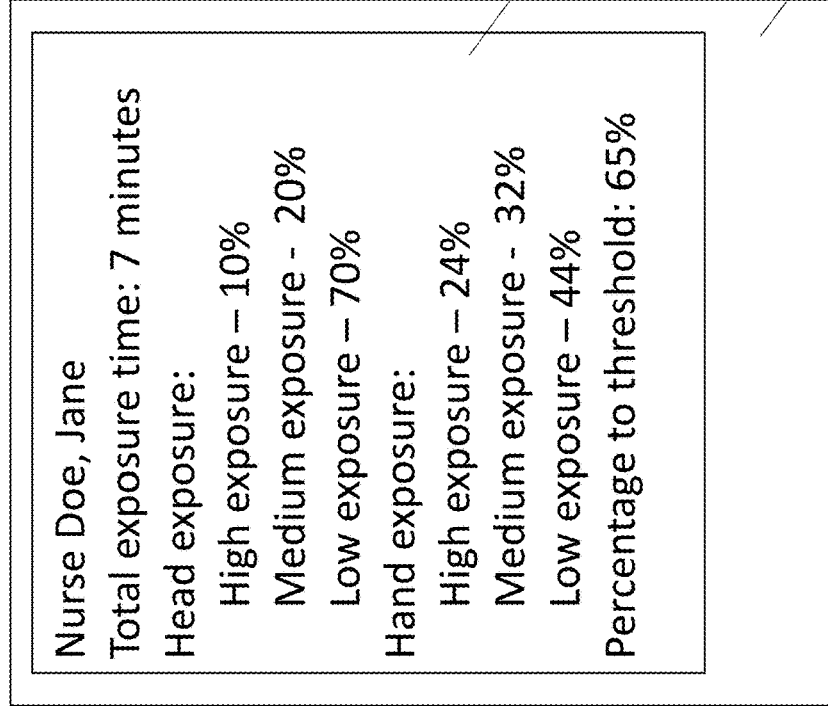
FIG. 15B is another exemplary exposure report.
Figure 15A:
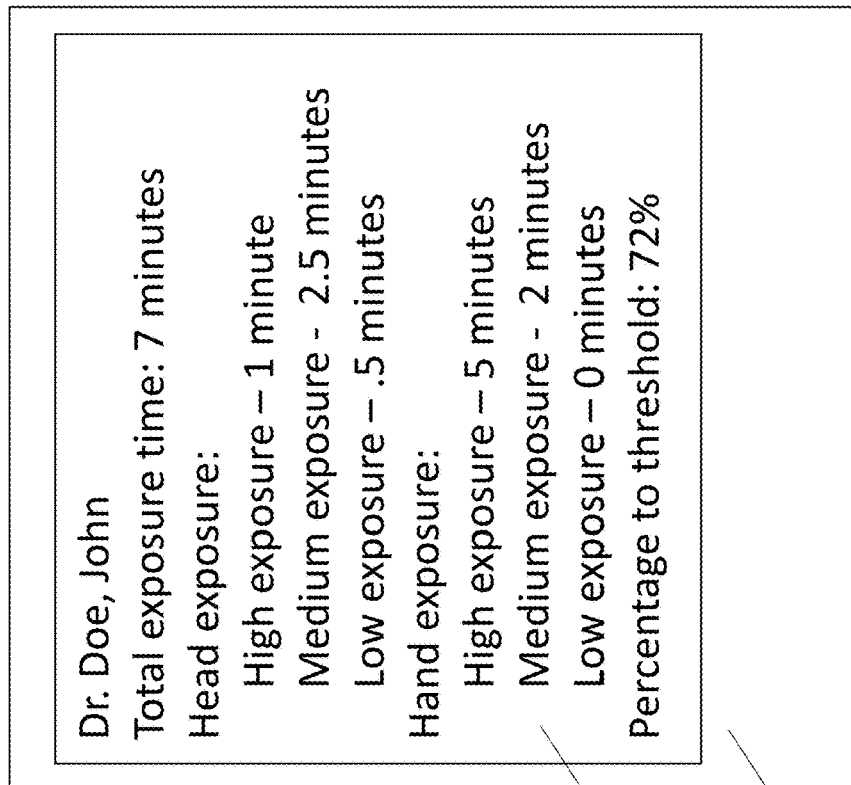
FIG. 15A is an exemplary exposure report in accordance with the present invention.

In exemplary embodiments, the visualization 50 may be provided only when the equipment 100 is active. Active may include, for example without limitation, one or more of being powered on, prepared for operation, emitting radiation, cooling down, some combination thereof, or the like. The visualization 50 may be provided for a margin of time before and/or after the equipment 100 is active. In other exemplary embodiments, the visualization 50 may be provided at all times. When the equipment 100 is active, or within the margin of time before and/or after being active, the visualization 50 may be changed. For example, without limitation, the visualization 50 may comprise a visible warning message, flashing, change of color, change of transparency, audible message, some combination thereof, or the like when the equipment 100 is active, or within the margin of time before and/or after being active. FIG. 15A and FIG. 15B illustrate exemplary exposure reports 200. Each exposure report 200 may comprise estimated relative exposure information for one or more persons. The exposure reports 200 may be generated, in whole or part, by the controller 56 in response to gathered data such as, but not limited to, exposure data and/or position data. Alternatively, or additionally, the exposure reports 200 may be generated, in whole or part, by data gathered directly from the various devices such as but not limited to, the AR tracking devices 46, the tracking devices 36, radiation exposure tracking devices 32, position tracking devices 57, some combination thereof, or the like. Alternatively, or additionally, the data from the controller 56 and/or the various devices may be transmitted to one or more remote databases for storage.

The exposure reports 200 may comprise identifying information for each individual such as but not limited to names, titles, photos, some combination thereof, or the like. The exposure reports 200 may comprise total estimated relative exposures information as well as estimated relative exposure information specific to certain parts of the body, such as but not limited to, head, arm, legs, torso, hands, feet, eyes, some combination thereof, or the like. Each category of estimated relative exposure (total and/or body part specific) may be broken down by areas of high, medium, and low relative radiation intensity exposure. Each category of exposure may be expressed as a time measurement, a percentage of total exposure time, some combination thereof, or the like.

The exposure reports 200 may comprise a percentage or other indication of progress towards a threshold, goal, or the like for a time period, such as the year, month, quarter, or the like.

Figure 16:
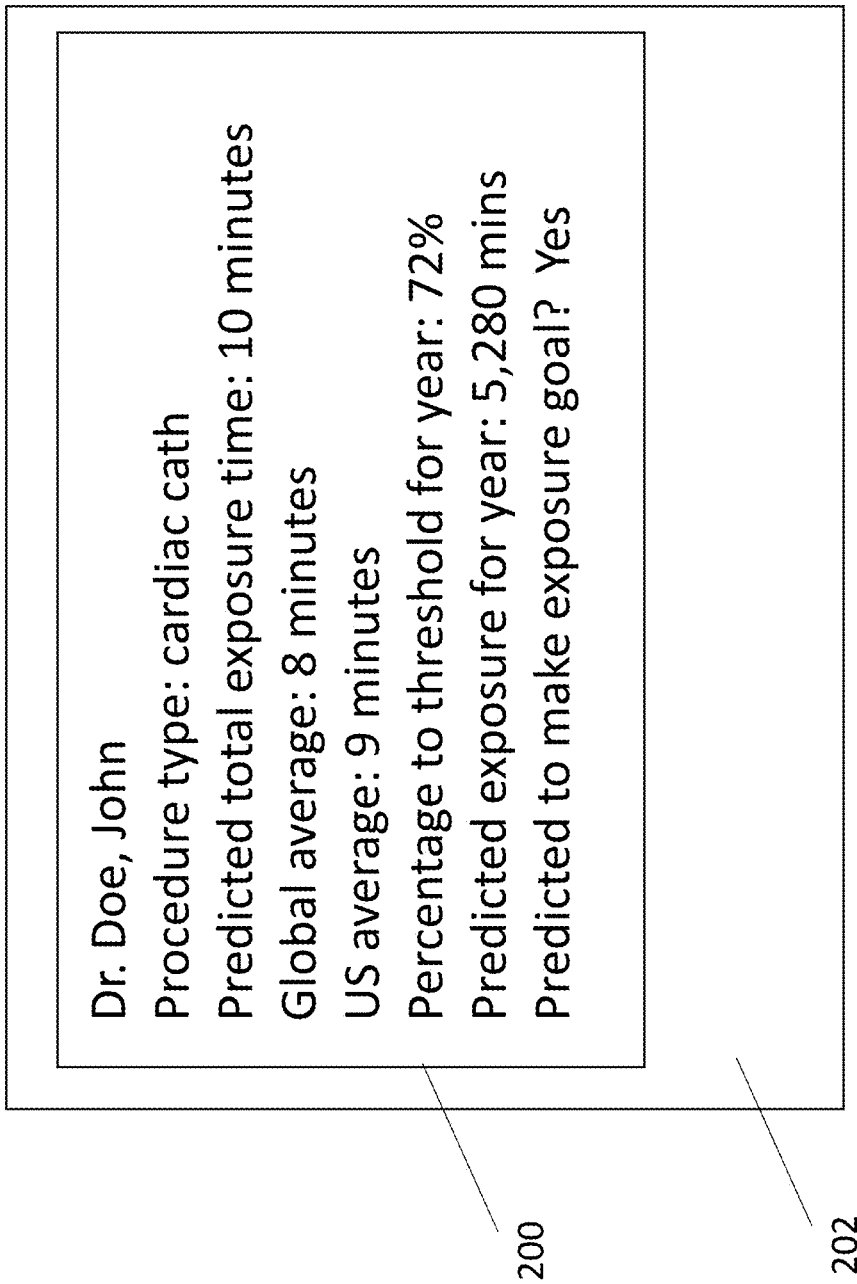
FIG. 16 is an exemplary predicted exposure report in accordance with the present invention.

FIG. 16 illustrates an exemplary predicted exposure report 300. Each predicted exposure report 300 may comprise estimated and/or predicted relative exposure information for one or more persons. The predicted exposure reports 300 may be generated by the controller 56 in response to gathered data such as, but not limited to, exposure data and/or position data. Alternatively, or additionally, the predicted exposure reports 300 may be generated, in whole or part, by data gathered directed from the various devices such as but not limited to, the AR tracking devices 46, the tracking devices 36, radiation exposure tracking devices 32, the position tracking devices 57, some combination thereof, or the like.

The predicted exposure reports 300 may comprise identifying information for the individual such as but not limited to name, title, photo, some combination thereof, or the like. The predicted exposure reports 300 may comprise procedure description information such as but not limited to name, CPT code, some combination thereof, or the like. The predicted exposure reports 300 may comprise a predicted total exposure time for the procedure. The predicted total exposure time may be based on average exposure during the same or similar procedures for the same person, facility averages, global averages, country specific averages, some combination thereof, or the like.

The predicted exposure reports 300 may comprise a percentage or other indication of progress towards a threshold for a time period, such as the year. The predicted exposure reports 300 may comprise predicted estimated total relative exposure for the time period, which may be expressed in a unit of time. The predicted exposure reports 300 may comprise a prediction of whether the reported individual will be under the threshold for the time period, such as but not limited to, a yes or no.

Information in the predicted exposure reports 300 may be determined by, entirely or in part, machine learning or other artificial intelligence software stored at the controller 56 or elsewhere. For example, without limitation, the individual's scheduled or predicted procedures for the year, as noted by CPT code or otherwise, may be retrieved and exposure time may be extrapolated based on personal averages, worldwide averages, country averages, facility averages, some combination thereof, or the like to determine total predicted exposure for the year. Each time a person using the disclosed systems or methods performs a procedure, the relative radiation intensity and/or related data may be stored at the controller 56 or elsewhere and associated with the procedure information, such as but not limited to by CPT code, such that said data may be utilized as part of the exposure reports 200, predicted exposure reports 300, machine learning or other artificial intelligence software, some combination thereof, or the like.

The exposure reports 200 and/or the predicted exposure reports 300, or data regarding the same, may be electronically communicated to one or more electronic devices 202 for display. The electronic devices 202 may comprise the electronic display 72, computers, tablets, smartphones, some combination thereof, or the like. The electronic devices 202 may be configured to generate all, or some, or the exposure reports 200 and/or predicted exposure reports 300.

The controller 56 and/or the electronic devices 202 may be configured to generate an alert when various exposure thresholds and/or predicted exposure thresholds are reached. Such thresholds may comprise yearly, monthly, or other time period limits, goals, or the like. For example, when 50% to the limit, 90% to the limit, and/or 100% to the limit is reached, an alert may be generated and transmitted. The recited thresholds are merely exemplary and are not intended to be limiting, any threshold or goal metric may be utilized. Such alerts may be transmitted as electronic notifications, audible messages (such as but not limited to from the speakers 59), displayed information at the AR tracking devices 46, displayed information at the electronic display 72, displayed information at the electronic devices 202, text messages, emails, automated calls, some combination thereof, or the like.

Several features and other aspects of the disclosures provided herein describe actions taken by the controller 56. However, it is contemplated that at least some of these actions may be determined, executed, or otherwise performed by controllers, processors, or other programmable logic devices located at the various devices such as but not limited to, the AR tracking devices 46, the projection devices 62, the tracking devices 36, the electronic display 80, other devices remote from the controller 56, some combination thereof, or the like.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing devices. The electronic devices may comprise personal computers, smartphone, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A system for providing a visualization of scattered radiation in an operating room in real time, said system comprising:
    a number of augmented reality ("AR") tracking devices, each associated with one of a number of individuals working in the operating room, and each comprising:
        a body attachment portion configured to facilitate securement to a portion of a body of the one of the individuals;
        a display portion comprising a transparent or translucent material and configured to display one or more images for the one of the individuals to view as an overlay to the operating room; and
        a position tracking device; and
    a controller in electronic communication with each of the AR tracking devices and comprising executable software instructions stored at one or more electronic storage devices, which when executed, configure one or more processors to:
        receive a location for the visualization of the scattered radiation;
        receive position data from each of the AR tracking devices;
        generate the visualization at the display portion of each of the AR tracking devices associated with position data indicating that a view of one of the individuals is directed towards the location, wherein the visualization comprises one or more shapes surrounding at least a portion of an operating table and an imaging device, and wherein the visualization is displayed in a fashion which reflects the position data for each AR tracking device, respectively;
        receive new position data from one of the AR tracking devices; and
        update said visualization at the display portion of the one of the AR tracking devices to reflect the new position data such that said visualization appears to be fixed at the location to the one of the individuals associated with the one of the AR tracking devices as a position of the one of the individuals changes.

2. The system of claim 1 further comprising:
    a position sensor provided at the imaging device, wherein said imaging device is configured to rotate about said operating table; and
    additional software instructions at the one or more electronic storage devices of said controller, which when executed, configure said one or more processors of said controller to:
        receive position data from said position sensor associated with said imaging device;
        use said received position data for said imaging device to determine said location;

receive new position data from said position sensor indicating movement of said imaging device; and adjust said visualization at each of said AR tracking devices to reflect the new position data for said imaging device.

3. The system of claim 2 further comprising:

a position sensor provided at the operating table, wherein said operating table is height adjustable; and additional software instructions at the one or more electronic storage devices of said controller, which when executed, configure said one or more processors of said controller to:

receive position data from said position sensor associated with said operating table;

use said received position data for said operating table to determine said location;

receive new position data from said position sensor associated with said operating table; and adjust said visualization at each of said AR tracking devices to reflect the new position data for the operating table.

4. The system of claim 1 wherein:

said body attachment portion of each of said AR tracking devices is configured to be secured to a human head; and said display portion comprises a surface configured to extend in front of a human eye when said body attachment portion is secured to the human head.

5. The system of claim 1 further comprising:

an interface provided at said controller for accepting user input; and additional software instructions at the one or more electronic storage devices of said controller, which when executed, configure said one or more processors of said controller to:

receive user input regarding a patient height and a patient weight; and adjust said visualization at each of said AR tracking devices to reflect the patient height and the patient weight.

6. The system of claim 5 further comprising:

additional software instructions at the one or more electronic storage devices of said controller, which when executed, configure said one or more processors of said controller to:

receive input regarding a type of the imaging device;

retrieve radiation scatter data specific to said type of the imaging device; and adjust said visualization at each of said AR tracking devices to reflect the retrieved radiation scatter data.

7. The system of claim 1 wherein:

said visualization is displayed in a semi-transparent fashion such that said operating room is visible through said visualization; and said visualization comprises a multi-layered sphere wherein a first layer of said sphere has a first diameter and comprises a first color and a second layer of said sphere has a second diameter which is larger than the first diameter and comprises a second color.

8. The system of claim 1 wherein:

said visualization is displayed in a semi-transparent fashion such that said operating room is visible through said visualization; and said visualization comprises a multi-layered cloud wherein a first layer of said cloud comprises shapes at a first density, and a second layer comprises said shapes at a second density which is greater than said first density.

9. The system of claim 1 further comprising:

a radiation exposure measurement device located at each of the AR tracking devices; and additional software instructions at the one or more electronic storage devices of said controller, which when executed, configure said one or more processors of said controller to:

receive radiation measurements from each of the radiation exposure measurement devices; and associate each received radiation measurement with one of the individuals associated with one of the AR tracking devices from which the measurement is received.

10. The system of claim 9 further comprising:

additional software instructions at the one or more electronic storage devices of said controller, which when executed, configure said one or more processors of said controller to adjust said visualization at each of said AR tracking devices to reflect the received radiation measurements.

11. The system of claim 1 further comprising:

multiple position measurement devices, each located at different portions of each of the bodies of the individuals; and additional software instructions at the one or more electronic storage devices of said controller, which when executed, configure said one or more processors of said controller to:

receive position measurements from each of the position measurement devices; and generate a report comprising relative radiation intensity exposure for each of the different portions of the bodies of the individuals, wherein higher levels of relative radiation intensity are reported for parts of the bodies of the individuals closer to the imaging device.

12. A method for providing a visualization of scattered radiation in an operating room in real time, said method comprising the steps of:

providing a controller in electronic communication with a number of holographic projection devices within the operating room;

receiving position data from a position sensor of an imaging device within the operating room;

receiving position data from a position sensor of an operating table, wherein said imaging device is moveable about said operating table, and wherein said operating table is moveable;

generating the visualization of the scattered radiation in a three-dimensional, semi-transparent form about the imaging device and the operating table, wherein said visualization is specific to the position of the imaging device relative to the operating table;

repositioning the imaging device or the operating table;

receiving new position data form the position sensor of the imaging device or position sensor of the operating table; and adjusting the visualization to reflect the new position data.

13. The method of claim 12 further comprising the steps of:

receiving data regarding the type of the imaging device, wherein the visualization generated is specific to the type of the imaging device.

14. The method of claim 12 wherein:
said visualization comprises a multi-layered cloud wherein a first layer of said cloud comprises a first color and a second layer of said cloud, which extends beyond the first layer, comprises a second color.

15. The method of claim 12 further comprising the steps of:
receiving user input regarding a patient height and a patient weight at a user interface for said controller; and
adjusting said visualization to reflect the patient height and the patient weight.

16. The method of claim 12 further comprising the steps of:
receiving position data from position tracking devices, each associated with one of a number of individuals in the operating room; and
generating a report indicating high, medium, and low relative radiation intensity exposure time for each of the individuals, wherein the high relative radiation intensity exposure level is recorded for a given one of the individuals where the position data indicates that the given one of the individuals was within a first distance of the imaging device, wherein the medium relative radiation intensity exposure level is recorded for a given one of the individuals where the position data indicates that the given one of the individuals was located beyond the first distance but within a second distance of the imaging device, and wherein the low relative radiation intensity exposure level is recorded where the position data for a given one of the individuals indicates that the given one of the individuals was located beyond the second distance but within a third distance of the imaging device.

17. A system for providing a visualization of scattered radiation in an operating room in real time, said system comprising:
an electronic display within the operating room;
a number of tracking devices, each associated with one of a number of individuals working in the operating room, each of said tracking devices comprising:
a body attachment portion configured to facilitate securement to a portion of a body of the one of the individuals; and
a position tracking device; and
a controller in electronic communication with each of the tracking devices and comprising executable software instructions stored at one or more electronic storage devices which when executed configure one or more processors to:
receive position data from each of the tracking devices;
generate the visualization of the scattered radiation at the electronic display about a representation of an operating table and imaging device; and
generate a representation of each of the individuals at the electronic display to represent positions of the individuals relative to the visualization as determined from the position data received from each of the tracking devices;
wherein said visualization comprises a multi-layered sphere or cloud wherein a first portion of said sphere or cloud comprises a first color, a second portion of said sphere or cloud which extends beyond said first portion and comprises a second color, and a third layer of said sphere or cloud which extends beyond said second layer and comprises a third color.

18. The system of claim 17 further comprising:
a display portion provided at each of the tracking devices, wherein each of said display portions comprise a transparent or translucent material and is configured to display one or more images in an augmented reality fashion; and
additional software instructions at the one or more electronic storage devices, which when executed, configure said one or more processors to generate the visualization at the display portions of each of the tracking devices from which position data is received indicating a direction of gaze towards said operating table or said imaging device, wherein said visualization is displayed in a semi-transparent fashion such that said visualization is visible and said patient is visible through said visualization.

19. The system of claim 17 further comprising:
a number of holographic projection devices in electronic communication with the controller; and
additional software instructions at the one or more electronic storage devices, which when executed, configure said one or more processors to instruct said projection devices to generate said visualization within said operating room in a manner which is visible by an unaided eye.

20. The system of claim 17 further comprising:
a first position sensor located at said operating table;
a second position sensor located at a radiation producing pieces of medical equipment;
an interface provided at said controller for accepting user input; and
additional software instructions at the one or more electronic storage devices, which when executed, configure said one or more processors to:
receive position data from said first and second position sensors;
adjust said visualization at said electronic display to reflect the position of the operating table and the medical equipment;
receive input regarding a type of medical equipment;
receive user input regarding a patient height and a patient weight; and
adjust said visualization to reflect the type of medical equipment, the patient height, and the patient weight.

21. A system for providing a visualization of scattered radiation in an operating room in real time, for use during a medical procedure, said system comprising:
a controller having executable software instructions stored at one or more electronic storage devices, which when executed, configure one or more processors to:
process data inputs from a user pertaining to locations of at least radiation causing equipment and a patient in the operating room;
compute three-dimensional data for the expected location and intensity of the scattered radiation in the operating room based on the input data and stored data of at least one radiation scatter diagram pertaining to said equipment; and
from said three-dimensional data, generate the visualization of the scattered radiation in the operating room; and
a projector system in electronic communication with the controller for projecting mapping on surfaces of the room the visualization in the operating room in substantially real time such that one or more medical professionals in the room may see the visualization and position themselves to lessen their physical interaction within zones of the visualization.

22. The system of claim 21 wherein:
the visualization is moved in substantially real time as the equipment or the patient is moved in the operating room during the medical procedure.

* * * * *